(12) United States Patent
Bonnette et al.

(10) Patent No.: US 10,869,990 B2
(45) Date of Patent: Dec. 22, 2020

(54) INFUSION CATHETER WITH HIGH PRESSURE CAPABILITIES

(71) Applicant: BOSTON SCIENTIFIC SCIMED, INC., Maple Grove, MN (US)

(72) Inventors: Michael J. Bonnette, Minneapolis, MN (US); Michael P. Schrom, Forest Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 578 days.

(21) Appl. No.: 15/649,200

(22) Filed: Jul. 13, 2017

(65) Prior Publication Data

US 2018/0015255 A1 Jan. 18, 2018

Related U.S. Application Data

(60) Provisional application No. 62/362,016, filed on Jul. 13, 2016.

(51) Int. Cl.
| | |
|---|---|
| *A61M 25/00* | (2006.01) |
| *A61M 5/142* | (2006.01) |
| *A61B 17/3203* | (2006.01) |
| *A61M 25/01* | (2006.01) |
| *A61M 25/09* | (2006.01) |

(52) U.S. Cl.
CPC ... *A61M 25/0074* (2013.01); *A61B 17/32037* (2013.01); *A61M 5/142* (2013.01); *A61M 25/005* (2013.01); *A61M 25/007* (2013.01); *A61M 25/0023* (2013.01); *A61M 25/0105* (2013.01); *A61M 25/09* (2013.01)

(58) Field of Classification Search
CPC .............. A61M 25/0074; A61M 25/09; A61M 25/007; A61M 25/0079; A61M 5/142
See application file for complete search history.

(56) References Cited

U.S. PATENT DOCUMENTS

| | | | |
|---|---|---|---|
| 5,957,901 A | * | 9/1999 | Mottola .............. A61M 25/007 604/264 |
| 7,226,433 B2 | | 6/2007 | Bonnette et al. |
| 8,162,877 B2 | | 4/2012 | Bonnette et al. |
| 8,998,843 B2 | | 4/2015 | Bonnette et al. |

(Continued)

FOREIGN PATENT DOCUMENTS

| | | |
|---|---|---|
| CN | 1802184 A | 7/2006 |
| CN | 103096826 A | 5/2013 |

(Continued)

OTHER PUBLICATIONS

Invitation to Pay Additional Fees dated Oct. 30, 2017 for International Application No. PCT/US2017/041957.

*Primary Examiner* — Jason E Flick
*Assistant Examiner* — Tasnim Mehjabin Ahmed
(74) *Attorney, Agent, or Firm* — Seager, Tufte & Wickhem, LLP (57) ABSTRACT

An infusion catheter is disclosed. An example infusion catheter includes an elongate tubular member having a proximal portion and a distal portion, wherein the distal portion includes an infusion region extending along a portion thereof. Further, the infusion region of the elongate tubular member includes a plurality of apertures, and the apertures reduce the surface area of the infusion region by 0.25%-10%.

19 Claims, 5 Drawing Sheets

(56) References Cited

U.S. PATENT DOCUMENTS

| | | | |
|---|---|---|---|
| 9,078,691 B2 | 7/2015 | Morris et al. | |
| 2005/0124969 A1* | 6/2005 | Fitzgerald | A61B 5/0084 |
| | | | 604/508 |
| 2007/0106245 A1* | 5/2007 | McQueen | A61M 25/09 |
| | | | 604/508 |
| 2008/0188831 A1 | 8/2008 | Bonnette et al. | |
| 2011/0190731 A1* | 8/2011 | Massengale | A61M 25/0074 |
| | | | 604/523 |
| 2014/0155830 A1 | 6/2014 | Bonnette et al. | |
| 2014/0155862 A1 | 6/2014 | Baxter et al. | |

FOREIGN PATENT DOCUMENTS

| | | |
|---|---|---|
| EP | 0788774 A1 | 8/1997 |
| EP | 2424606 A1 | 3/2012 |
| EP | 2712559 A2 | 4/2014 |
| WO | 2004083817 A2 | 9/2004 |
| WO | 2011139589 A2 | 11/2011 |

\* cited by examiner

INFUSION CATHETER WITH HIGH PRESSURE CAPABILITIES

CROSS-REFERENCE TO RELATED APPLICATIONS

This application claims the benefit of priority under 35 U.S.C. § 119(e) to U.S. Provisional Application No. 62/362,016, filed Jul. 13, 2016, the entire disclosure of which is herein incorporated by reference.

TECHNICAL FIELD

The disclosure is directed to infusion catheters and accessory devices for use with catheters. More particularly, the disclosure is directed to devices to aid in removing or accelerating the removal of thrombus.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example infusion catheter includes an elongate tubular member having a proximal portion and a distal portion, wherein the distal portion includes an infusion region extending along a portion thereof. Further, the infusion region of the elongate tubular member includes a plurality of apertures, and the apertures reduce the surface area of the infusion region by 0.25%-10%.

Alternatively or additionally to any of the embodiments above, wherein the distal portion of the tubular member further includes an inner surface, an outer surface and a wall extending therebetween, and wherein each of the plurality of apertures extends through the wall.

Alternatively or additionally to any of the embodiments above, wherein the plurality of apertures are uniformly spaced around the outer surface of the tubular member.

Alternatively or additionally to any of the embodiments above, wherein the plurality of apertures are configured to permit fluid under pressure up to 18,000 psi to flow therethrough.

Alternatively or additionally to any of the embodiments above, wherein the elongate tubular member is a metal, a glass or both metal and glass.

Alternatively or additionally to any of the embodiments above, further comprising a tip member, and wherein the tip member is positioned distal of the infusion region.

Alternatively or additionally to any of the embodiments above, wherein the tip member includes a coil.

Alternatively or additionally to any of the embodiments above, wherein the proximal portion of the elongate tubular member is configured to releasably attach to a fluid infusion system.

Alternatively or additionally to any of the embodiments above, further comprising an accessory device slidably and rotationally disposed within the catheter lumen.

Alternatively or additionally to any of the embodiments above, wherein the accessory device is configured to selectively restrict flow through one or more of the apertures.

Alternatively or additionally to any of the embodiments above, wherein the accessory device comprises a guidewire.

Alternatively or additionally to any of the embodiments above, wherein the proximal portion of the catheter extends along a longitudinal axis and the distal portion of the catheter is configured to extend at an angle to the longitudinal axis.

Alternatively or additionally to any of the embodiments above, wherein the angle is in the range of 1 to 90°.

Alternatively or additionally to any of the embodiments above, wherein the angle is in the range of 15 to 25°.

Alternatively or additionally to any of the embodiments above, wherein the angle is approximately 20°.

Another example infusion catheter comprises:

an elongate tubular member having a distal portion and a longitudinal axis, the distal portion including an infusion region;

wherein the infusion region has a surface area defined by a circumference of the tubular member and a length along the longitudinal axis of the tubular member;

wherein the infusion region includes a plurality of apertures located therein;

wherein the apertures reduce the surface area of the infusion region by 0.25%-10%;

wherein each of the plurality of apertures defines a surface area, and wherein the sum of the surface areas of the plurality of apertures is 0.0020 cm$^2$ to 0.0040 cm$^2$.

Alternatively or additionally to any of the embodiments above, wherein a proximal portion of the catheter extends along a longitudinal axis and the distal portion of the catheter is configured to extend at an angle to the longitudinal axis.

Alternatively or additionally to any of the embodiments above, further comprising an accessory device slidably and rotationally disposed within the catheter lumen.

Alternatively or additionally to any of the embodiments above, wherein the accessary device is configured to selectively restrict flow through one or more of the apertures.

Another example infusion catheter comprises:

an elongate tubular member having a proximal portion and a distal portion, wherein the distal portion includes an infusion region extending along a portion thereof; and an accessory device slidably and rotationally disposed within the catheter lumen, wherein the accessary device is configured to selectively restrict flow through one or more apertures located in the infusion region;

wherein the one or more apertures are configured to permit fluid to flow therethrough at a velocity in the range of 100 cm/sec to 200 cm/sec.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Infusion catheters and systems may be used to remove thrombus, plaques, lesions, clots, etc. from veins or arteries. These devices may be effective to remove acute thrombus but may be less effective on older or more organized thrombus, or areas of large clot burden such as that seen in deep vein thrombosis (DVT). It may be desirable to provide an infusion catheter designed to infuse high pressure jet streams of fluid (e.g., lytic agents) to flow therethrough. Additionally, it may be desirable to design an accessory device to be used in combination with the infusion catheter.

Figure 1:
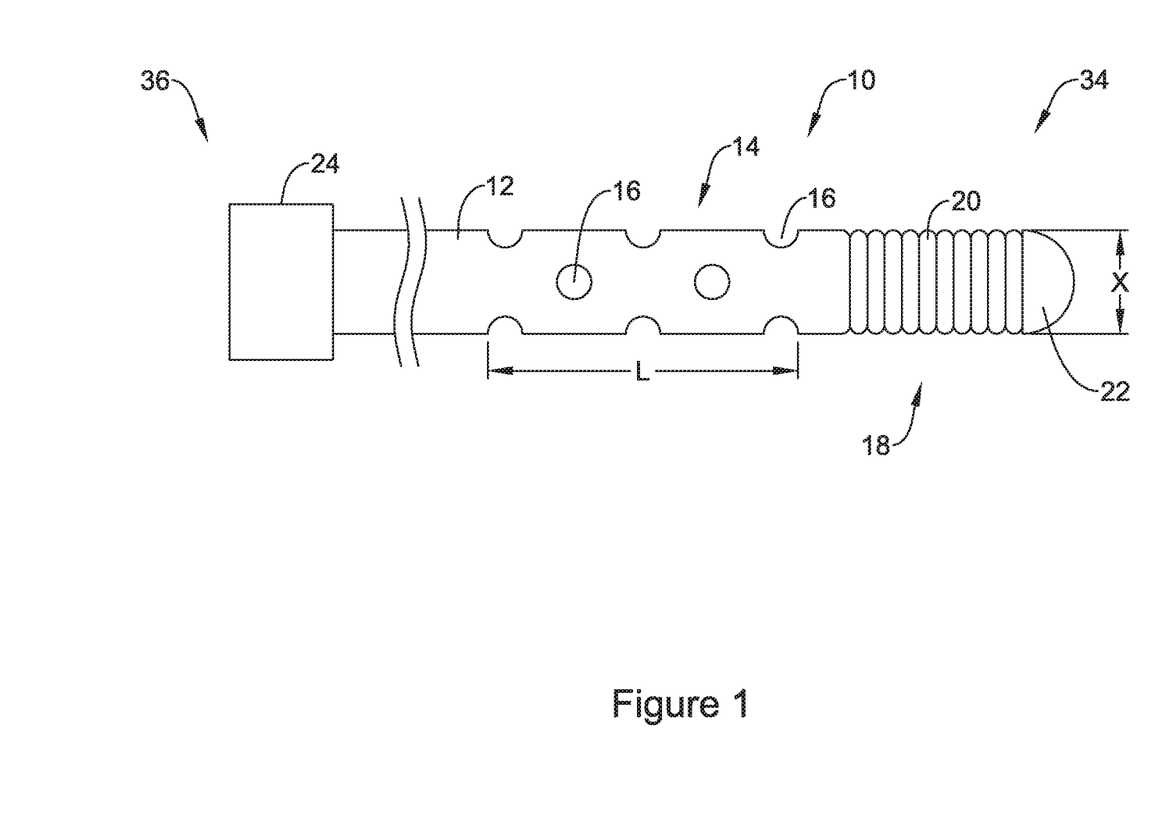
FIG. 1 illustrates an example infusion catheter.

FIG. 1 shows an example infusion catheter 10. Infusion catheter 10 may include an elongated tubular member 12 extending between a proximal portion 36 and a distal portion 34 of catheter 10. In at least some examples, infusion catheter 10 includes one or more apertures 16 positioned along distal portion 34. Additionally, infusion catheter may include a tip member 18 positioned distal to the one or more apertures 16. Tip member 18 may include a flexible coil member 20 and a distal tip portion 22. Distal tip portion 22 may be a solder tip. Tip portion 22 may have an outer diameter "X" as depicted in FIG. 1. Further, FIG. 1 illustrates that catheter 10 may include a handle member 24 attached to the proximal end 36 of catheter 10.

Tubular member 12 may include a lumen extending along a portion of or its entire length (e.g., the entire length of tubular member 12 from the proximal portion 36 to the distal portion 34). As will be described in greater detail below, the lumen of tubular member 12 may be in fluid communication with a fluid infusion system attached to the handle member 24. Handle member 24 may be releasably attached to a fluid infusion system attached thereto. Further, the lumen of tubular member 12 may permit fluid flow from the proximal portion 36 of tubular member 12 to one or more apertures 16 positioned along the distal portion 34 of tubular member 12.

Additionally, tubular member 12 may include an inner surface (e.g., an inner surface defining the lumen of tubular member 12) and an outer surface. Additionally, tubular member 12 may include a tubular wall extending between the inner surface and outer surface of the tubular member 12. It can further be appreciated that one or more apertures 16 may extend through the tubular wall. In other words, apertures 16 may permit fluid communication between the lumen of tubular member 12 and the outer surface of tubular member 12.

In some instances, the one or more apertures 16 disclosed above may define an infusion region 14. For purposes of this disclosure, the infusion region 14 may define a portion (e.g., region) along tubular member 12 within which one or more apertures 16 may positioned. In some examples, the infusion region 14 may extend partially or fully around the circumference of the tubular member 12. Further, the infusion region 14 may be defined along a given length along tubular member 12. For example, FIG. 1 shows an infusion region 14 defined by the length "L" in FIG. 1. In other words, FIG. 1 defines an infusion region as the portion of tubular member 12 in which apertures 16 are located within length "L" and spaced around the outer circumference of tubular member 12.

While FIG. 1 shows apertures 16 as being spaced equidistant from each other, it is contemplated that apertures 16 may be configured in a variety of patterns, arrangements, spacing, geometries, distributions, etc. In some examples, apertures 16 may be unequal distances from one another.

Additionally, in some examples apertures 16 may include more or fewer than the number of apertures 16 depicted in FIG. 1. For example, an example infusion region 14 may include 1, 2, 3, 4, 5, 6, 7, 8, 9, 10, 15, 20, 30, 40, 50, 100, 500, 1,000, 5,000, 10,000 or more apertures 16 arranged in a variety of patterns.

It can be further appreciated from FIG. 1 and the discussion above that each aperture 16 illustrated in FIG. 1 may include an area, or opening, through which infusion fluid (e.g., lytic) may flow (via the lumen of tubular member 12). Further, it can be appreciated that apertures 16, collectively, may define an area through which infusion fluid may flow. The collective area through which fluid may flow for apertures 16 may be calculated by adding the area of each individual aperture 16 located in infusion region 14.

For purposes of discussion herein, the "shape" of apertures 16 may be defined as the shape of apertures 16 as outlined on the outer surface of tubular member 12. For example, it can be appreciated that the "shape" of the apertures 16 shown in FIG. 1 is circular. In some examples, the "shape" of apertures 16 may be referred to as the "cross-sectional shape" of the apertures 16. While the shape of the apertures 16 shown in FIG. 1 are depicted as circular, it is contemplated that apertures 16 may be any shape or combinations of shapes. For example, apertures 16 may be circular, rectangular, oval, triangular, square, etc. and combinations thereof.

As discussed above, in some instances it may be desirable to utilize the example infusion catheters disclosed herein to treat diseased tissue. For example, in some instances it may be desirable infuse a lytic agent into an occlusion present in a body lumen. Further, in some examples it may be desirable to infuse a lytic agent into an occlusion under relatively high pressure. In other words, the examples disclosed herein may include infusion catheters in which a fluid (e.g., lytic agent) may be pumped into the lumen of tubular member 12 via an infusion injection system. The fluid may travel through the lumen of tubular member 12 to apertures 16, whereby the fluid may pass from the lumen of tubular member 12, through apertures 16 and into diseased tissue.

As stated above, in some instances it may be desirable to pass fluid from catheter 10 (via apertures 16) under high pressure. In some instances, the pressure under which fluid is infused through apertures 16 may be 1 psi to 18,000 psi.

Further, it can be appreciated that several design characteristics of catheter 10 may directly affect the pressure, flow rate (e.g., velocity), energy, etc. at which a fluid may pass through apertures 16. For example, it can be appreciated that the size (e.g., area), both individually and collectively, of apertures 16 may contribute to the pressure, flow rate (e.g., velocity), energy, etc. at which a fluid may pass through apertures 16. Additionally, the maximum infusion rate of the infusion system injecting fluid into the catheter 10 may directly affect the pressure, flow rate (e.g., velocity), energy, etc. at which a fluid may pass through apertures 16. Specifically, the velocity at which the fluid passes through apertures 16 may be a function of the total number of apertures 16 present in the infusion zone, the area of each of the apertures 16 and the maximum infusion rate imparted by the system 10. For example the velocity of the fluid exiting apertures 16 may be calculated as:

$$\text{Velocity} = \frac{Q}{A}$$

where,

Q=maximum infusion rate of fluid into catheter

A=total area of all apertures=[(area of each aperture)×(total number of apertures)].

To achieve the velocity suitable for treatment of the diseased tissue contemplated herein, the diameter of individual apertures 16 may be 0.000254 cm to 0.004826 cm, or about 0.001270 cm to 0.004572 cm, or about 0.002540 cm to 0.004318 cm, or about 0.003810 cm.

Further, as stated above, it is contemplated herein that that the total number of apertures 16 present in the infusion zone may range from 1 to more than 10,000 apertures 16, or about 10 to 750 apertures 16, or about 100 to 500 apertures 16 or about 300 apertures 16.

Additionally, in at least some examples disclosed herein, the maximum infusion rate of fluid imparted to catheter 10 may be from about 0.0045 cm$^3$/sec to about 3.25 cm$^3$/sec, or from about 0.450 cm$^3$/sec to about 2.80 cm$^3$/sec, from about 0.900 cm$^3$/sec to about 2.25 cm$^3$/sec, or about 0.50 cm$^3$/sec.

Therefore, from the above ranges for the maximum infusion rate, the total number of apertures and the area of individual apertures, the range of velocities at which a fluid may pass through apertures 16 may be from about 0.622 cm/sec to about 314,200 cm/sec, or from about 10 cm/sec to about 50,000 cm/sec, or from about 100 cm/sec to about 1,000 cm/sec, or about 150 cm/sec.

Figure 2:
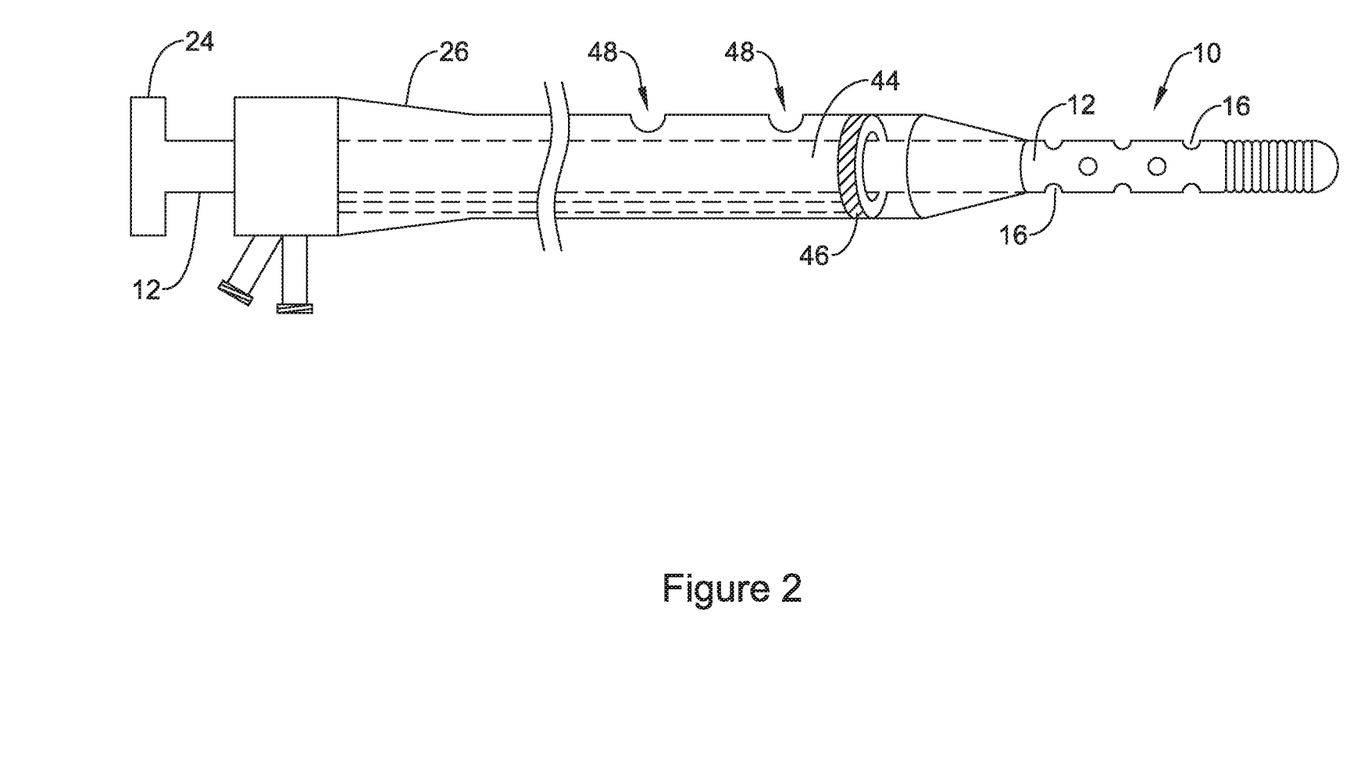
FIG. 2 illustrates the example infusion catheter of FIG. 1 extending within a thrombectomy catheter.

As discussed above, it may be desirable to attach infusion catheter 10 to a fluid infusion system and/or thrombectomy system. For example, FIG. 2 illustrates a thrombectomy system that may include a tubular catheter shaft 44, a fluid jet emanatory 46, one or more opening(s) 48 along the side wall of the catheter shaft, etc. An example thrombectomy system can be found in U.S. Pat. No. 8,162,877, the entirety of which is incorporated by reference. Other suitable thrombectomy systems may include The AngioJet Infusion Systems, available from Boston Scientific.

FIG. 2 further illustrates example infusion catheter 10 (including tubular member 12) extending through the thrombectomy system 26. It can be appreciated from FIG. 2 that tubular member 12 may extend the length of the system 26. For example, FIG. 2 illustrates the distal portion of catheter 10 extending away from the distal end of the catheter 26 and the proximal portion of catheter 10 extending from the proximal portion of the catheter 26. Additionally, FIG. 2 illustrates that tubular member 12 may be manipulated via the control handle 24 attached to the proximal portion of tubular member 12.

In some instances it may be desirable to select (e.g., customize) specific apertures 16 in which fluid exits the infusion region 14. For example, it may be desirable to control the direction in which fluid flows out of infusion region 14 by blocking (e.g., covering) specific apertures 16, thereby allowing fluid to flow out of the remaining, unblocked (e.g., uncovered) apertures 16.

Figure 3:
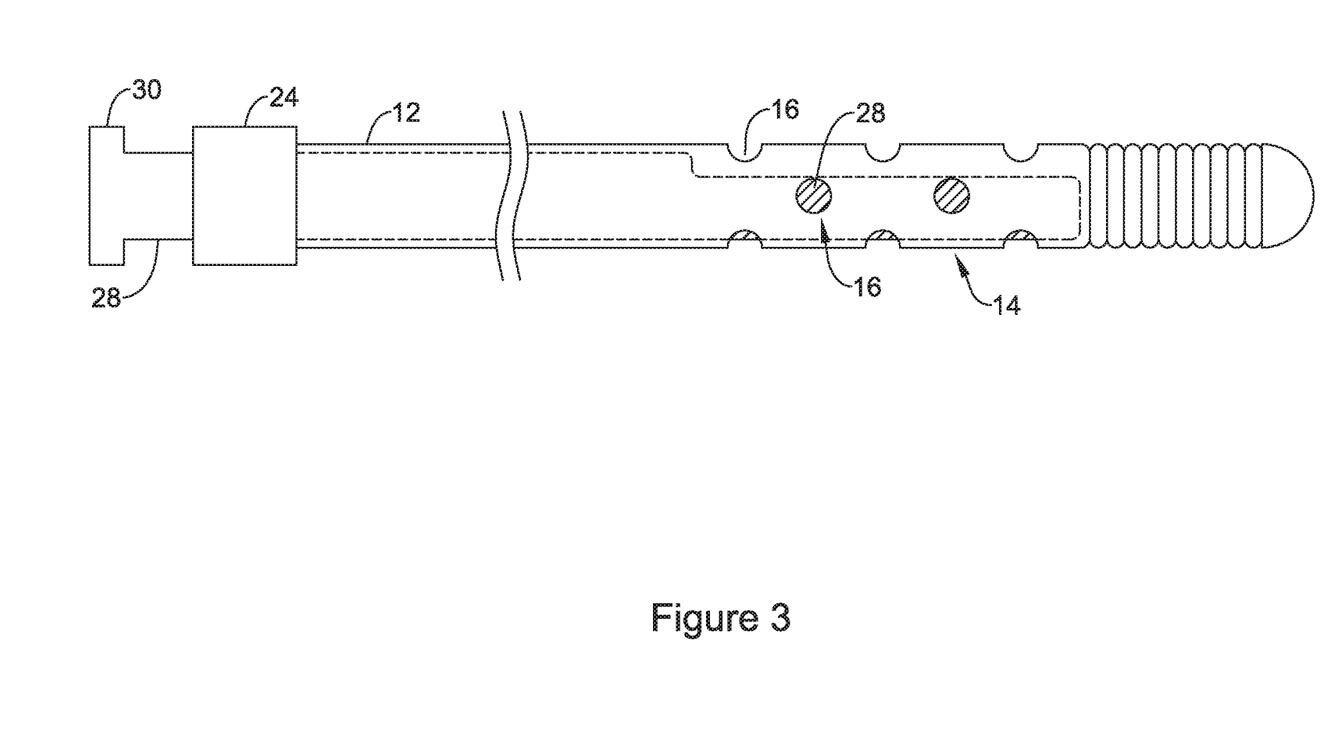
FIG. 3 illustrates an example infusion catheter.

FIG. 3 illustrates an example accessory device 28 and methodology for controlling the direction in which fluid flow from infusion region 14. In some examples, accessory device 28 may include a guidewire. In other examples, accessory device 28 may include a tubular member and/or catheter. For example, it is contemplated that accessory device 28 may include a guidewire having one or more apertures disposed along a distal region thereof.

As illustrated in FIG. 3, accessory device 28 may be inserted into the proximal end of tubular member 12 and advanced through the lumen of tubular member 12 to infusion region 14. FIG. 3 further illustrates that the distal end of accessory device 28 may selectively cover one or more apertures 16 (depicted by the hashed lines in FIG. 3). It can be appreciated that by covering various apertures 16, accessory device 28 may prevent fluid from flowing through selected apertures 16, while permitting fluid to flow through the remaining, uncovered apertures 16. The ability to select which apertures 16 from which fluid may flow may be beneficial to properly aligning and/or targeting diseased tissue. For example, it is contemplated that accessory device 28 may positioned such that only apertures 16 aligned on a single side of infusion region 14 are uncovered (and therefore, remain open to allow fluid to flow therethrough).

It can be appreciated that accessory device 28 may be both rotationally and/or longitudinally disposed within the lumen of tubular member 12. In other words, accessory device 28 may be able to be both rotated and translated with the lumen of tubular member 12. In some examples, a handle member 30 may be attached to the proximal region of accessory device 28. Handle member 30 may assist a clinician in manipulating accessory device 28. In other words, a clinician may utilize handle 30 to rotate and/or advance accessory device 28 with the lumen of tubular member 12.

Figure 4:
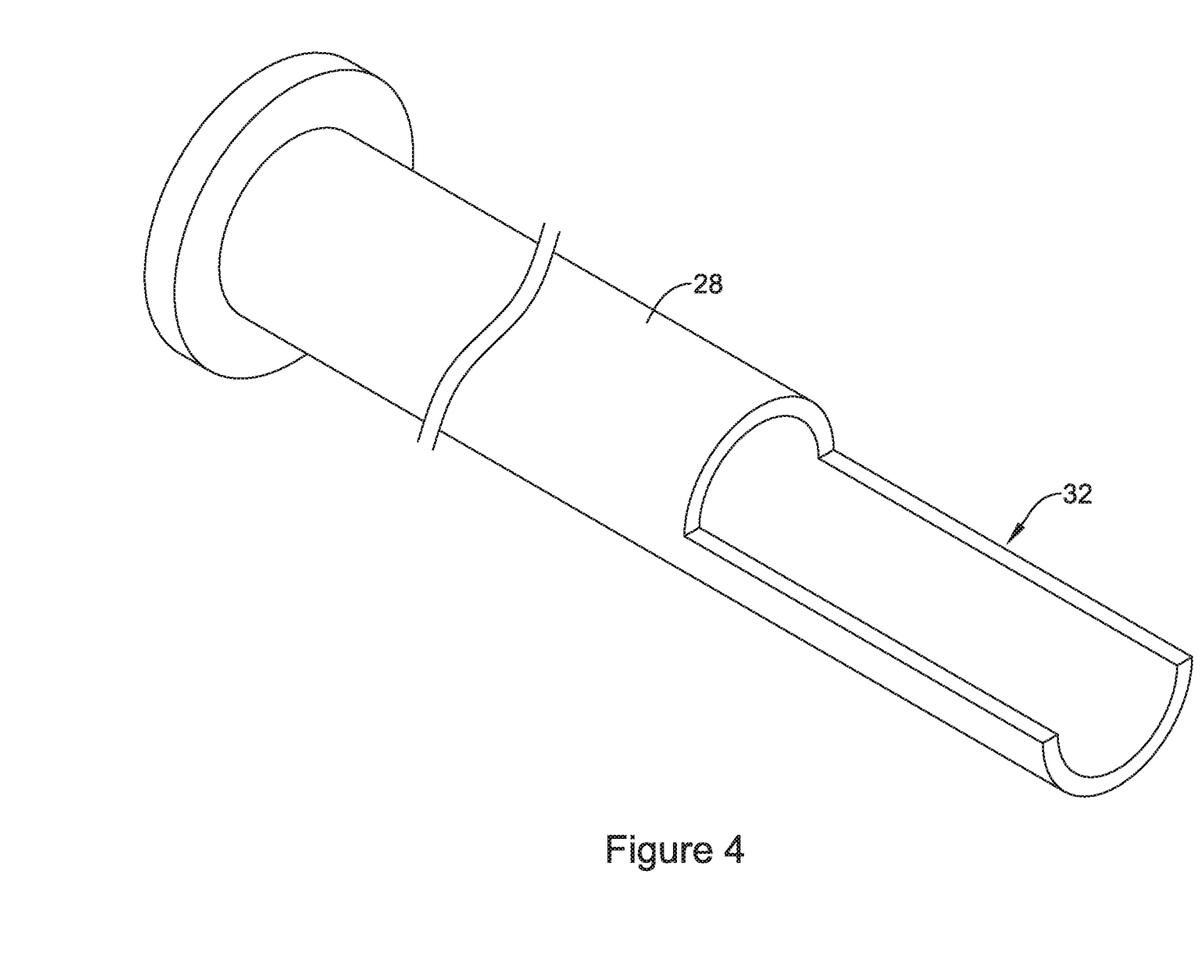
FIG. 4 illustrates an example accessory catheter.

FIG. 4 illustrates an example accessory device 28. As shown in FIG. 4, accessory device 28 may include a tubular member including or not including a lumen extending therein. Further, accessory device 28 may include a distal end region 32. In some examples, a portion of distal end region 32 may be removed from accessory device 28. For instance, in examples in which accessory device 28 include a lumen, a portion of the tubular wall of accessory device 28 may be removed to define the distal end region shape as illustrated in FIG. 4. In some instances, the shape of distal end region of FIG. 4 may resemble a "half-pipe."

It is noted that the shape of accessory device 28 illustrated in FIG. 4 is not intended to be limiting. Rather, accessory device 28 may be a variety of shapes and/or configurations. For example, in some examples, accessory device 28 may resemble a cylinder, tubular member, tubular member with one or more apertures, a tubular member with any portion of the tubular wall removed, or the like.

Additionally, it can be appreciated that the accessory device 28 may be utilized, designed, manipulated, and/or positioned such that any combination of apertures may be uncovered and/or selected to permit fluid to flow therethrough. For example, in some instances, accessory device 28 may be positioned such that 100% of the apertures are closed. In other examples, accessory device may be positioned such that 100% of the apertures are open. Additionally, it can be appreciated that accessory device 28 may be positioned such that any of the apertures may either be covered or uncovered, depending on the specific direction, flow rate, volume, pressure, etc. that is required to flow through infusion region 14.

Additionally, as discussed above, infusion region may be defined as an area bound by the length "L" along the tubular member 12 and the circumference of tubular member 12. It can further be appreciated that this infusion region may be represented (e.g., conceptualized) as a square have a surface area that is equal to the length "L" multiplied by the "Circumference of Tubular Member 12." Further, it can be appreciated that the area of the apertures 16 may reduce the surface area of the infusion region by a given percentage, based on the size and number of apertures present with the infusion zone. For example, the area of apertures 16 may reduce the surface are of the infusion region by 0.001, 0.01, 0.1, 1, 2, 3, 4, 5, 6, 7, 8, 9, 10, 15, 20, 30, 40, 50, 75 or more percent. Additionally, it can be appreciated that reducing the surface area of infusion region 14 by a given percentage (via apertures 16) may be correlate to a specific pressure, flow rate and/or volume of fluid flowing through the apertures 16 present in infusion region 14. For example, infusion region 14 may be designed such that the area of the apertures 16 reduce the surface area of the infusion region (discussed above) by 0.25% to 10%, or about 0.5% to 5%, or about 0.75% to 2%, or about 1%.

As discussed above, any of the example catheters 10 or accessory devices disclosed herein may be operated in a rotational and/or longitudinal motion, either via a motor or manually. Further, the infusion catheter examples disclosed herein may aid in the disruption of a clot or occlusion, which may additionally improve the evacuative and shearing properties of a thrombectomy catheter. Further, in some instances the accessory devices disclosed herein may also be designed to increase the diametrical zone in which fluid may be infused.

Figure 5:
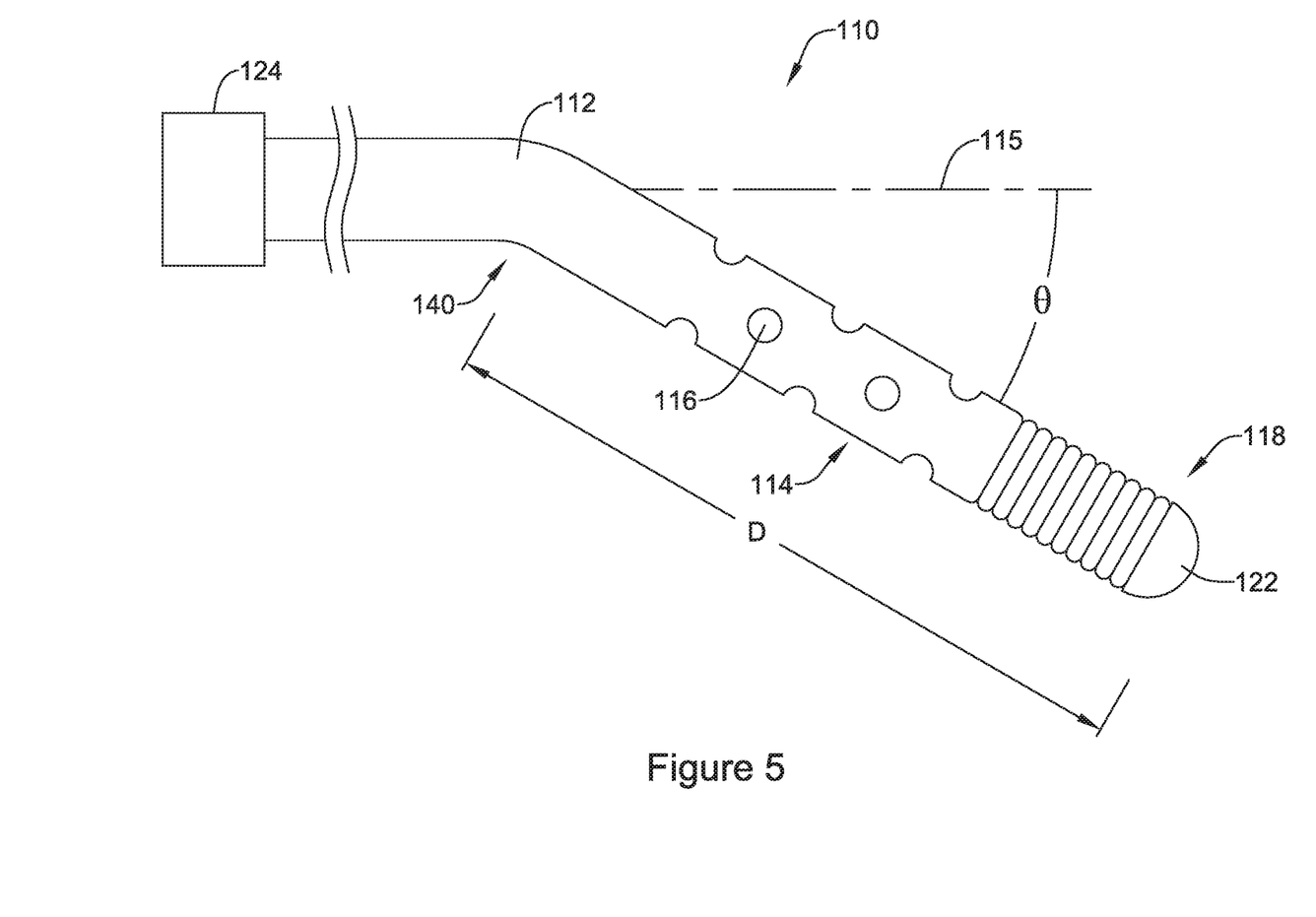
FIG. 5 illustrates an example infusion catheter.

In some instances, a predetermined bend may be placed at a particular distance from the distal tip of infusion catheter 10. For example, FIG. 5 shows an example infusion catheter 110 includes a predetermined bend 140 positioned a length "D" from the end of distal tip member. It is noted that catheter 110 may be similar in form and function to other catheters disclosed herein. For example, catheter 110 may include a tubular member 112 and an infusion region 114. The location and degree of curvature of this bend 140 may dictate the amount of deflection of infusion region 114. Additionally, as described above, handle 124 may be provided at the proximal end 136 of catheter 110 to rotate the catheter 110 in a circular sweeping action to gain greater coverage within a larger vessel or to manipulate the path of the catheter 110.

FIG. 5 illustrates a distal portion of the catheter 110 including a predetermined bend 140. As depicted in FIG. 5, catheter 110 may include a longitudinal axis 115. Longitudinal axis 115 may be defined by the unbent portion of catheter 110. In other words, longitudinal axis 115 extends parallel to the unbent portion of catheter 110. The bend 140 may be positioned a distance "D" from the distal end of the tip member 118. In some instances, the bend 140 may be positioned in the range of 0 cm to 50 cm from the distal end. The bend angle θ, relative to the longitudinal axis 115, may be in the range of 1° to 90°, in the range of 10° to 30°, in the range of 15° to 25°, or approximately 20°. However, it is contemplated that the bend angle may be less than 1° or greater than 90°, as desired.

Additionally, as discussed above, in some instances catheter 110 may be used in conjunction with a fluid infusion system (e.g., a thrombectomy catheter). Therefore, when infusion catheter 110 is positioned within the lumen of an example thrombectomy catheter, the predetermined bend 140 may also be disposed within the lumen of the thrombectomy catheter. Further, the bend 140 may deflect the distal end region of the thrombectomy catheter. For example, the bend 140 may bias the portion of the catheter 110 and/or thrombectomy catheter that is distal to the bend towards a location offset from a longitudinal axis of the portion of the catheter 110 and/or thrombectomy catheter that is proximal to the bend. Deflecting the distal end region of the catheter 110 may increase the diametrical sweep coverage of the distal end region of catheter 110 and/or a thrombectomy catheter within which catheter 110 is positioned. For example, as the deflection angle θ increases, the diametrical sweep coverage of the distal end region of catheter 110 and/or a thrombectomy catheter within which catheter 110 is positioned may also increase. Additionally, deflection of distal end region may also bring the other structures and/or apertures of catheter 110 and/or the thrombectomy catheter (e.g., the inflow or outflow orifices of a thrombectomy catheter) closer to the thrombus to further facilitate removal of the tissue.

In some instances, the proximal end of catheter 110 may include a marker or indictor (not shown) to provide the user with information related to the circumferential location of the bend. As stated above, coil 120 may be disposed over a length of the core wire adjacent to the distal end. A tip member 118 having a generally curved, atraumatic, shape, such as a solder tip 122, may be formed on the core wire at or adjacent to the distal end. A portion of the coil 120 may be coupled to the tip 122. In some instances, a portion of the coil 120 may be embedded within the tip 122. Embedded is understood to be disposed within, coupled to, set in, implanted, fixed, etc. The tip 122 may, thus, fix the coil 120 relative to core wire. Alternatively, the coil 120 may be soldered to core wire proximate to the tip 122. In some instances, the coil 120 may be replaced with a slotted tube or other flexible member.

The catheter 10 or components thereof may be comprised of nickel-titanium alloy, stainless steel, a composite of nickel-titanium alloy and stainless steel, and/or include nickel-cobalt-chromium-molybdenum alloy (e.g., MP35-N). Alternatively, the catheter 10 or components thereof may be comprised of metals, polymers, combinations or composites thereof, or other suitable materials. In some instances, a portion or all of the catheter 10 or components thereof may be radiopaque to allow the catheter 10 or components thereof to be viewed on a fluoroscopy screen, or other imaging technique, during a procedure. In some instances, the distal end and/or coil may be radiopaque to aid the physician in determining the location of the distal end of the catheter 10 or components thereof.

The materials that can be used for the various components of the catheter 10 and/or other devices disclosed herein may include those commonly associated with medical devices. For simplicity purposes, the following discussion makes reference to accessory devices and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An infusion catheter, comprising:
   an elongate tubular member having a proximal portion and a distal portion, wherein the distal portion includes an infusion region extending along a portion thereof;
   wherein the infusion region of the elongate tubular member includes a plurality of apertures;
   wherein the apertures reduce a surface area of the infusion region by 0.25%-10%;
   wherein the total number of apertures is greater than or equal to 100; and
   wherein each of the plurality of apertures includes a diameter, and wherein the diameter is less than or equal to 0.0048 cm.

2. The infusion catheter of claim 1, wherein the distal portion of the elongate tubular member further includes an inner surface, an outer surface, and a wall extending therebetween, and wherein each of the plurality of apertures extends through the wall.

3. The infusion catheter of claim 2, wherein the plurality of apertures are spaced equidistant around the outer surface of the elongate tubular member.

4. The infusion catheter of claim 1, wherein the plurality of apertures are configured to permit fluid under pressure up to 18,000 psi to flow therethrough.

5. The infusion catheter of claim 1, wherein the elongate tubular member is a metal, a glass, or both metal and glass.

6. The infusion catheter of claim 1, further comprising a tip member, and wherein the tip member is positioned distal of the infusion region.

7. The infusion catheter of claim 6, wherein the tip member includes a coil.

8. The infusion catheter of claim 1, wherein the proximal portion of the elongate tubular member is configured to releasably attach to a fluid infusion system.

9. The infusion catheter of claim 1, further comprising an accessory device slidably and rotationally disposed within the elongate tubular member.

10. The infusion catheter of claim 9, wherein the accessory device is configured to selectively restrict flow through one or more of the apertures.

11. The infusion catheter of claim 10, wherein the accessory device comprises a guidewire.

12. An infusion catheter, comprising:
an elongate tubular member having a distal portion and a longitudinal axis, the distal portion including an infusion region;
wherein the infusion region has a surface area defined by a circumference of the elongate tubular member and a length along the longitudinal axis of the tubular member;
wherein the infusion region includes a plurality of apertures located therein;
wherein the apertures reduce the surface area of the infusion region by 0.25%-10%;
wherein each of the plurality of apertures defines a surface area, and wherein the sum of the surface areas of the plurality of apertures is 0.0020 cm$^2$ to 0.0040 cm$^2$;
wherein the total number of apertures is greater than or equal to 100; and
wherein each of the plurality of apertures includes a diameter, and wherein the diameter is less than or equal to 0.0048 cm.

13. The infusion catheter of claim 12, wherein the proximal portion of the catheter extends along a longitudinal axis and the distal portion of the catheter is configured to extend at an angle to the longitudinal axis.

14. The infusion catheter of claim 13, wherein the angle is in the range of 1° to 90°.

15. The infusion catheter of claim 13, wherein the angle is in the range of 15° to 25°.

16. The infusion catheter of claim 13, wherein the angle is approximately 20°.

17. The infusion catheter of claim 12, wherein a proximal portion of the catheter extends along a longitudinal axis and the distal portion of the catheter is configured to extend at an angle to the longitudinal axis.

18. The infusion catheter of claim 12, further comprising an accessory device slidably and rotationally disposed within a lumen of the elongate tubular member.

19. The infusion catheter of claim 12, wherein the accessory device is configured to selectively restrict flow through one or more of the apertures.

* * * * *